United States Patent
Lee et al.

(10) Patent No.: US 7,839,134 B2
(45) Date of Patent: Nov. 23, 2010

(54) METHOD AND APPARATUS FOR SIMULTANEOUSLY DETECTING SIZE AND CONCENTRATION OF IONIC MATERIAL

(75) Inventors: Kyu-sang Lee, Yongin-si (KR); Kyu-tae Yoo, Yongin-si (KR); Jeo-young Shim, Yongin-si (KR); Won-seok Chung, Yongin-si (KR); Yeon-ja Cho, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 994 days.

(21) Appl. No.: 11/619,650

(22) Filed: Jan. 4, 2007

(65) Prior Publication Data

US 2007/0251301 A1 Nov. 1, 2007

(30) Foreign Application Priority Data

Mar. 31, 2006 (KR) ...................... 10-2006-0029807

(51) Int. Cl.
*G01N 27/00* (2006.01)
(52) U.S. Cl. ...................................... 324/71.1; 205/775
(58) Field of Classification Search ................ 324/71.1, 324/76.11; 205/775
See application file for complete search history.

(56) References Cited

U.S. PATENT DOCUMENTS 4,238,757 A 12/1980 Schenck 4,397,714 A * 8/1983 Janata et al. ................. 205/775

OTHER PUBLICATIONS

EP Search Report dated Apr. 11, 2008, Application 06125701.0-2204 Samsung Electronic.
XP000848941 "The How and Why of Electronic Noses", Sep. 1998.
XP004708527 Craven, et al. "Electronic noses—development . . . ", 1996.
XP000297731 Gardner, et al. "Detection of Vapours and Odours . . . ", Jul. 1992.
XP000516380 Horner G. "Signalverabeitung Bei Chemosensorarrays" *EP Search report should serve as "concise statement", 1995.
XP006013140 Hines, et al. "Electronic noses: a review of signal . . . ", Dec. 1999.
EP 1217364 (Seiko Epson), Jun. 26, 2002.

* cited by examiner

*Primary Examiner*—Vincent Q Nguyen
(74) *Attorney, Agent, or Firm*—Cantor Colburn LLP (57) ABSTRACT

A method for simultaneously detecting a size and concentration of ionic materials includes measuring voltage drop values of at least three ionic materials of which sizes and concentrations are known using each of at least two FET-based sensors having different electrical characteristics, determining at least three points in a three-dimensional plot from the known sizes, concentrations and the measured voltage drop values, approximating the at least three points into a single plane, measuring a voltage drop value of an ionic material of which size and concentration are unknown using the at least two FET-based sensors, determining equipotential lines existing on the plane using the voltage drop value of the unknown ionic material and determining a cross point between each of the equipotential lines.

20 Claims, 5 Drawing Sheets

METHOD AND APPARATUS FOR SIMULTANEOUSLY DETECTING SIZE AND CONCENTRATION OF IONIC MATERIAL

This application claims priority to Korean Patent Application No. 10-2006-0029807, filed on Mar. 31, 2006, and all the benefits accruing therefrom under 35 U.S.C. §119, the contents of which are incorporated herein in its entirety by reference.

BACKGROUND OF THE INVENTION

1. Field of the Invention

The present invention relates to a method and apparatus for simultaneously detecting a size and concentration of an ionic material.

2. Description of the Related Art

Transistor-based biosensors are a kind of sensor for detecting ionic materials, especially, biomolecules, using electrical signals. Transistor-based biosensors are manufactured through semiconductor manufacturing processes and have the advantage of high speed electrical signal transition so that many studies involving them have been conducted.

U.S. Pat. No. 4,238,757 is the original patent relating to the detection of a biological response using a field effect transistor ("FET"). This patent relates to a biosensor detecting an antigen-antibody reaction by way of a current change of semiconductor inversion layer occurring due to a change in surface charge concentration. This patent relates to the detection of a protein among biomolecules.

The advantages of using a FET as a biosensor are lower costs, high-speed sensing and a simpler combination of integrated circuit ("IC")/micro-electro mechanical systems ("MEMS") process, compared to conventional methods.

On a surface of a gate electrode of a FET based biosensor, probe biomolecules may or may not be fixed. A detecting method for biomolecules using a FET-based biosensor involves a measuring current or voltage change due to the binding of a target biomolecule to the surface of the gate electrode to which probe biomolecules ma or may not be fixed. In an alternative method, the detecting method can be performed by measuring the current or voltage change due to the presence of a target biomolecule within a certain distance from a gate electrode to which no probe biomolecules are fixed.

However, when conventional FET-based biosensors are used to detect a target ionic material, the biosensors can detect only a concentration of unspecified ionic materials due to a voltage or current change, however, there is a problem in that it cannot be ascertained whether the target ionic materials is responsible for the voltage or current change.

When a primer is accurately selected and assay conditions are accurately set in order that a specific polymerase chain reaction ("PCR") should be ideally performed in advance, the existence of target nucleic acid can be fully confirmed from only the existence of bands. However, when PCR is actually performed using an unknown sample, reactants obtained under second-best conditions instead of the optimum conditions are detected, and thus errors can frequently occur.

Therefore, there is a need for simultaneously measuring the concentration and size of ionic particles, for example, a length of nucleic acid, in order to determine whether an error has occurred or not.

BRIEF SUMMARY OF THE INVENTION

An exemplary embodiment provides a method of simultaneously detecting a size and concentration of an ionic material.

An exemplary embodiment provides an apparatus for simultaneously detecting a size and concentration of an ionic material.

In an exemplary embodiment, there is provided a method of simultaneously detecting a size and concentration of ionic materials. The method includes measuring voltage drop values of at least three kinds of ionic materials of which sizes and concentrations are known using each of at least two FET-based sensors having different electrical characteristics for detecting ionic materials, determining at least three points in a three-dimensional plot, the points including a size, a concentration and a voltage drop value, from the known sizes, concentrations and the measured voltage drop values of the at least three kinds of ionic materials with respect to the each of at least the two FET-based sensors having different electrical characteristics for detecting ionic materials, approximating the at least the three points with a single plane with respect to the each of at least two FET-based sensors having different electrical characteristics for detecting the ionic materials, measuring a voltage drop value of ionic material of which size and concentration are unknown using the each of at least two FET-based sensors having different electrical characteristics for detecting the ionic materials, determining equipotential lines existing on the plane using a voltage drop value of the unknown ionic material with respect to the each of at least two FET-based sensors having different electrical characteristics for detecting the ionic materials and determining a cross point between at least two equipotential lines.

In an exemplary embodiment, the measuring voltage drop values includes introducing a solution containing each of the at least three ionic materials into a chamber including the each of at least two FET-based sensors having different electrical characteristics for detecting the ionic materials.

In an exemplary embodiment, the different electrical characteristics of the each of at least FET-based sensors for detecting ionic materials are represented by a difference of materials on a surface of the sensor, a sensor structure or a size of the sensor.

In an exemplary embodiment, the each of at least two FET-based sensors for detecting ionic materials includes a plurality of FET-based sensors having the same electrical characteristics.

In an exemplary embodiment, the measuring voltage drop values of the at least three ionic materials includes averaging voltage drop values measured using the plurality of FET-based sensors having the same electrical characteristics.

In an exemplary embodiment, the size of the ionic materials is a charge or a length of the ionic materials.

In an exemplary embodiment, the approximating the plane includes solving constants of a, b and c of Equation 1 using three points:

$$ax+by+cz+1=0 \qquad \text{Equation (1)}$$

where x refers to size of ionic materials, y refers to concentration and z refers to voltage drop value.

In an exemplary embodiment, the determining equipotential lines include substituting the voltage drop value of the unknown measured ionic material into Equation 1.

In an exemplary embodiment, the determining at least one cross point between the equipotential lines includes obtaining cross points between each two equipotential lines of at least three equipotential lines when at the least three equipotential lines exist and obtaining an average point of the cross points.

In an exemplary embodiment, the ionic materials are biomolecules.

In an exemplary embodiment, the biomolecules are nucleic acids or proteins.

In an exemplary embodiment, there is provided an apparatus for detecting a size and concentration of ionic materials. The apparatus includes a voltage drop measurement unit that includes at least two FET-based sensors having different electrical characteristics for detecting ionic materials, a point determination unit that determines points in a three-dimensional plot including a size, a concentration and a voltage drop value from known sizes, concentrations and voltage drop values, respectively, of the ionic materials measured in the voltage drop measurement unit, a plane approximation unit that approximates at least three points determined in the point determination unit into a single plane, an equipotential line determination unit that determines equipotential lines existing on the plane approximated in the plane approximation unit using the voltage drop values measured in the voltage drop measurement unit of ionic materials of which size and concentration are unknown and a cross point determination unit that determines a cross point between at least two equipotential lines determined in the equipotential line determination unit.

In an exemplary embodiment, the voltage drop measurement unit includes the each of at least two FET-based sensors having different electrical characteristics for detecting ionic materials in a single chamber.

In an exemplary embodiment, the different electrical characteristics of the each of at least two FET-based sensors for detecting ionic materials are represented by a difference of materials on a surface of the sensor, a sensor structure or a size of the sensor.

In an exemplary, the each of at least two FET-based sensors for detecting ionic materials includes a plurality of FET-based sensors having the same electrical characteristics.

In an exemplary embodiment, the size of the ionic materials is a charge or length of the ionic materials.

In an exemplary embodiment, the plane approximation unit solves constants of a, b and c of Equation 1 using the three points:

$$ax+by+cz+1=0 \qquad \text{Equation (1)}$$

where x refers to size of ionic materials, y refers to concentration and z refers to voltage drop value.

In an exemplary embodiment, the equipotential line determination unit substitutes the voltage drop value of the unknown measured ionic material into Equation 1.

In an exemplary embodiment, the cross point determination unit obtains cross points between each two equipotential lines of at least the three equipotential lines when at least three equipotential lines exist and obtains an average point of the cross points.

In an exemplary embodiment, the ionic materials are biomolecules.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Hereinafter, the present invention will be described in greater detail with reference to accompanying drawings.

Figure 1:
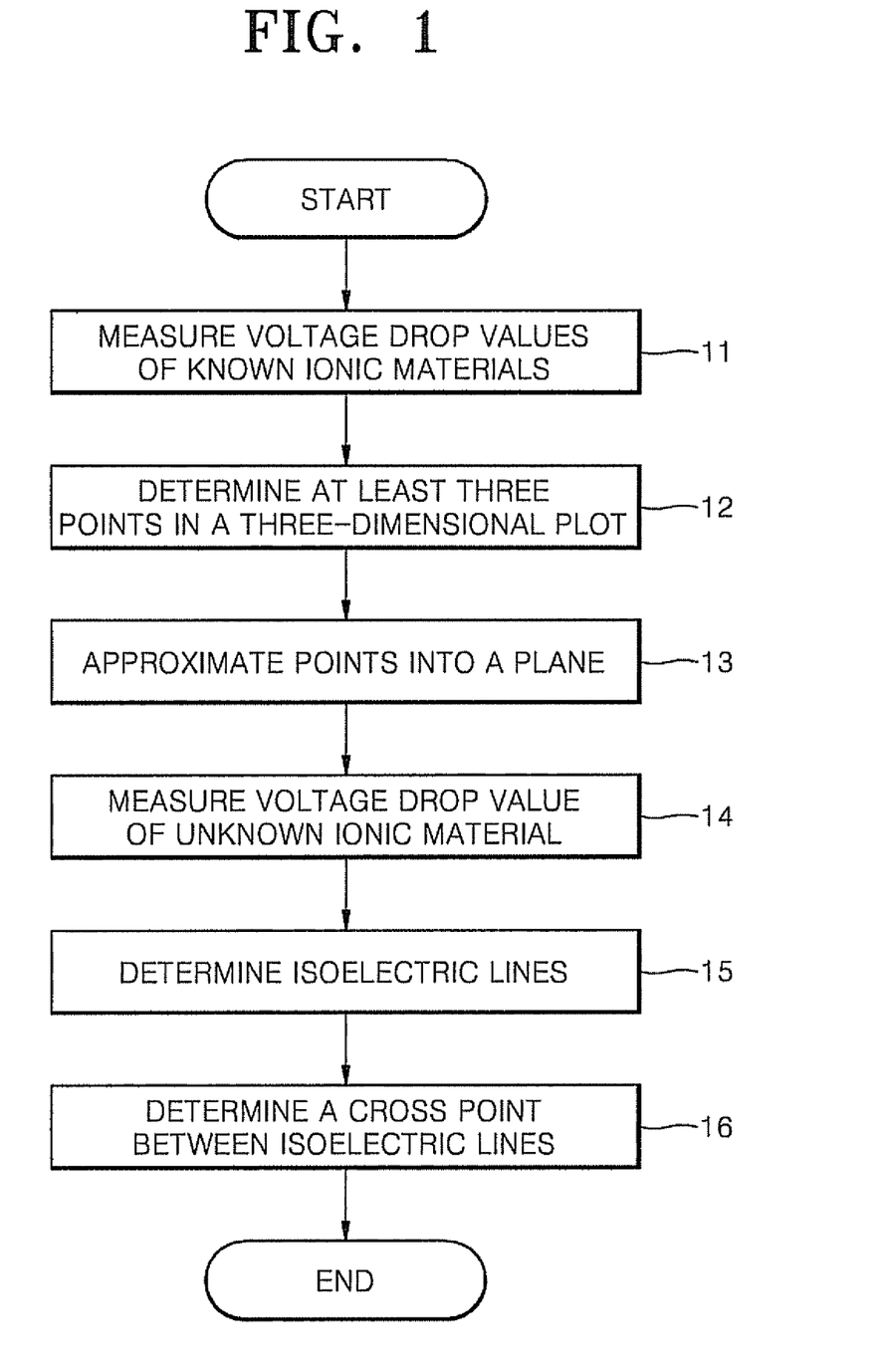
FIG. 1 is a flowchart illustrating an exemplary embodiment of a method of detecting a size and concentration of an ionic material according to the present invention.

FIG. 1 is a flowchart illustrating an exemplary embodiment of a method of detecting a size and concentration of an ionic material according to the present invention.

Referring to FIG. 1, measurement of voltage drop values of at least three kinds of ionic materials of which sizes and concentrations are known (11) is performed using each of at least two FET-based sensors having different electrical characteristics.

In an exemplary embodiment, the measurement of voltage drop values of the ionic materials (11) may be performed by introducing solutions each containing one of the ionic materials in a chamber. The chamber includes at least two FET-based sensors having different electrical characteristics for detecting ionic materials.

The different electrical characteristics of the FET-based sensors for detecting ionic materials may be obtained through a difference of a surface material of the sensor, a sensor structure and/or a size of the sensor. The difference of the sensor structure may be a relatively slight difference that occurs in a process of manufacturing the same sensor.

In an exemplary embodiment, the FET-based sensors for detecting ionic materials can independently include a plurality of FET-based sensors having substantially the same electrical characteristics. Voltage drop values of the ionic materials can be calculated by averaging voltage drop values measured using a plurality of FET-based sensors having the same electrical characteristics.

The FET can be any of a number of FETs, such as those used in a complementary metal-oxide semi-conductor ("CMOS") device, etc. The FET may be a n-type metal oxide semiconductor field-effect transistor ("n-MOS") or a p-channel metal-oxide semi-conductor field-effect transistor ("p-MOS"). In one exemplary embodiment, when a substrate of the FET is n-type doped, a source and a drain can be independently p-type doped. Alternatively, when the substrate is p-type doped, the source and drain can be independently n-type doped.

The ionic materials are not particularly limited, and may include, but are not limited to, ionic atoms, ionic molecules or biomolecules. The biomolecules can be nucleic acid selected from the group consisting of deoxyribonucleic acid ("DNA"), ribonucleic acid ("RNA"), peptide nucleic acid ("PNA"), locked nucleic acid ("LNA") and mixtures thereof, or protein selected from the group consisting of an enzyme, a substrate, an antigen, an antibody, a ligand, an aptamer and a receptor.

In exemplary embodiments, when the ionic material is an ion, a size of the ionic material is considered as the charge of the ion. When the ionic material is nucleic acid, the size of the ionic material is considered as the length of the nucleic acid.

Referring back to FIG. 1, next, determination of at least three points in a three-dimensional plot including a size, a concentration and a voltage drop value from the known sizes and concentrations and the measured voltage drop values corresponding to at least the three kinds of ionic materials (12) is performed with respect to each of at least two FET-based sensors having different electrical characteristics for detecting the ionic materials.

In an exemplary embodiment, the three-dimensional plot may include an x-axis set to size, a y-axis set to concentration and a z-axis set to voltage drop value. The determination of at least the three points (12) can be performed such that, a voltage drop value is determined using a kind of an ionic material of which a size and concentration are known, and the size, concentration and voltage drop value are represented in the three-dimensional plot. Next, points of the remaining two kinds of ionic materials are represented in the three-dimensional plot as the same method described above.

Approximation of a single plane using least the three points (13) is performed with respect to at least two FET-based sensors having different electrical characteristics for detecting ionic materials.

The plane approximation operation (13) may include any of a number of known statistical methods of plane approximation and is not particularly limited.

In one exemplary embodiment, when three points are approximated into a single plane, the plane approximation can be performed by solving three constants, such as a, b and c of Equation 1. By this, Equation 1 including three variables, such as x, y and z, can be obtained.

$$ax+by+cz+1=0 \qquad \text{Equation (1)}$$

where x refers to the size of ionic materials, y refers to concentration of the ionic materials and z refers to voltage drop value of the ionic materials.

Measurement of voltage drop value of ionic material of which size and concentration are unknown (14) is performed using each of at least two FET-based sensors having different electrical characteristics for detecting ionic materials.

In an exemplary embodiment, the measurement of voltage drop value of the ionic material (14) may be performed by introducing solutions each containing one of the ionic materials in a chamber including at least two FET-based sensors having different electrical characteristics for detecting ionic materials.

The FET-based sensors for detecting ionic materials can independently include a plurality of FET-based sensors having the same electrical characteristics. Calculation of voltage drop values of the ionic materials may be performed by averaging voltage drop values calculated using a plurality of FET-based sensors having the same electrical characteristics.

A determination of equipotential lines that exist on the approximated plane (15) is performed using voltage drop values of the unknown ionic materials with respect to each of at least two FET-based sensors having different electrical characteristics for detecting ionic materials.

In one exemplary embodiment, when three points are approximated using a plane, determining the equipotential lines (15) may be performed by substituting z, a voltage drop value of the unknown calculated ionic materials, into Equation 1. By this, an equation comprising two variables of x and y can be obtained.

Then, determination of a cross point between at least the two equipotential lines (16) is performed.

Figure 2:
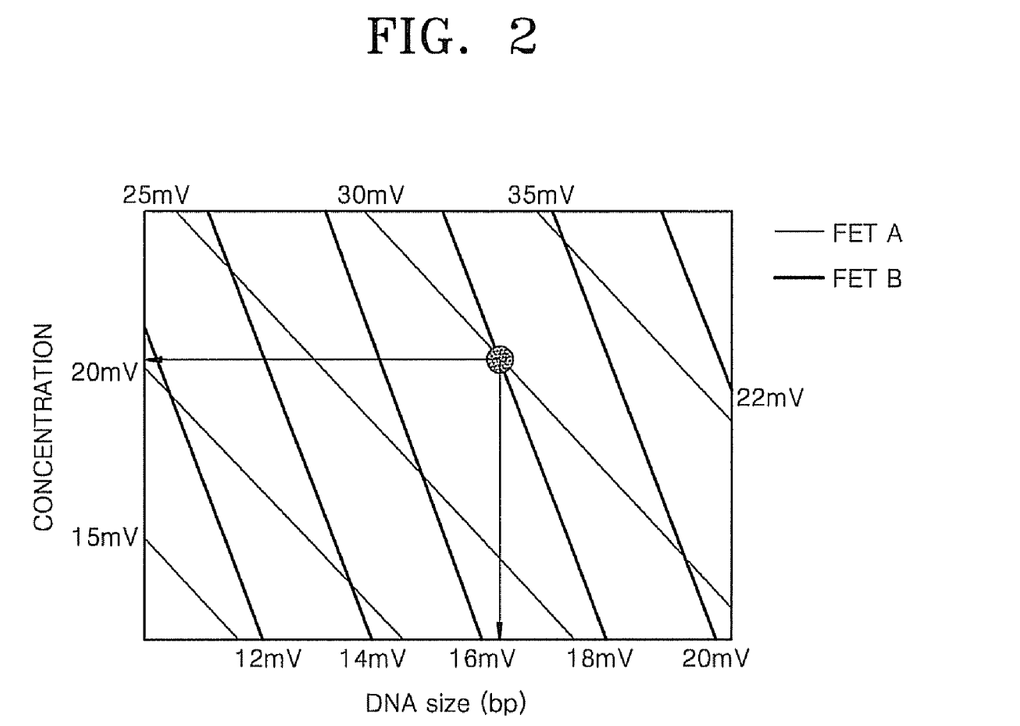
FIG. 2 is a graph illustrating an exemplary embodiment of a process of determining a cross point between equipotential lines according to the present invention.

FIG. 2 is a graph illustrating an exemplary embodiment of a process of determining a cross point between equipotential lines according to the present invention Referring to FIG. 2, equipotential lines are represented on a two-dimensional plane including DNA size base pair ("bp") on the x-axis and concentration on the y-axis. For FET A, 15 mV, 20 mV, 25 mV, 30 mV and 35 mV equipotential lines are illustrated. For FET B, 12 mV, 14 mV, 16 mV, 18 mV, 20 mV and 22 mV equipotential lines are illustrated.

When voltage drop values of DNA of which size and concentration are unknown with respect to FET A and FET B having different electrical characteristics for detecting ionic materials are 30 mV and 18 mV, respectively, two equipotential lines which cross are obtained and a cross point thereof is determined using the results. An x value and a y value of the cross point refers to the unknown DNA size ("bp") and the unknown DNA concentration, respectively.

Determination of the cross point can be performed such that when at least three equipotential lines exist, cross points between each two equipotential lines of the three equipotential lines are obtained, and an average of the cross points is obtained.

Figure 3:
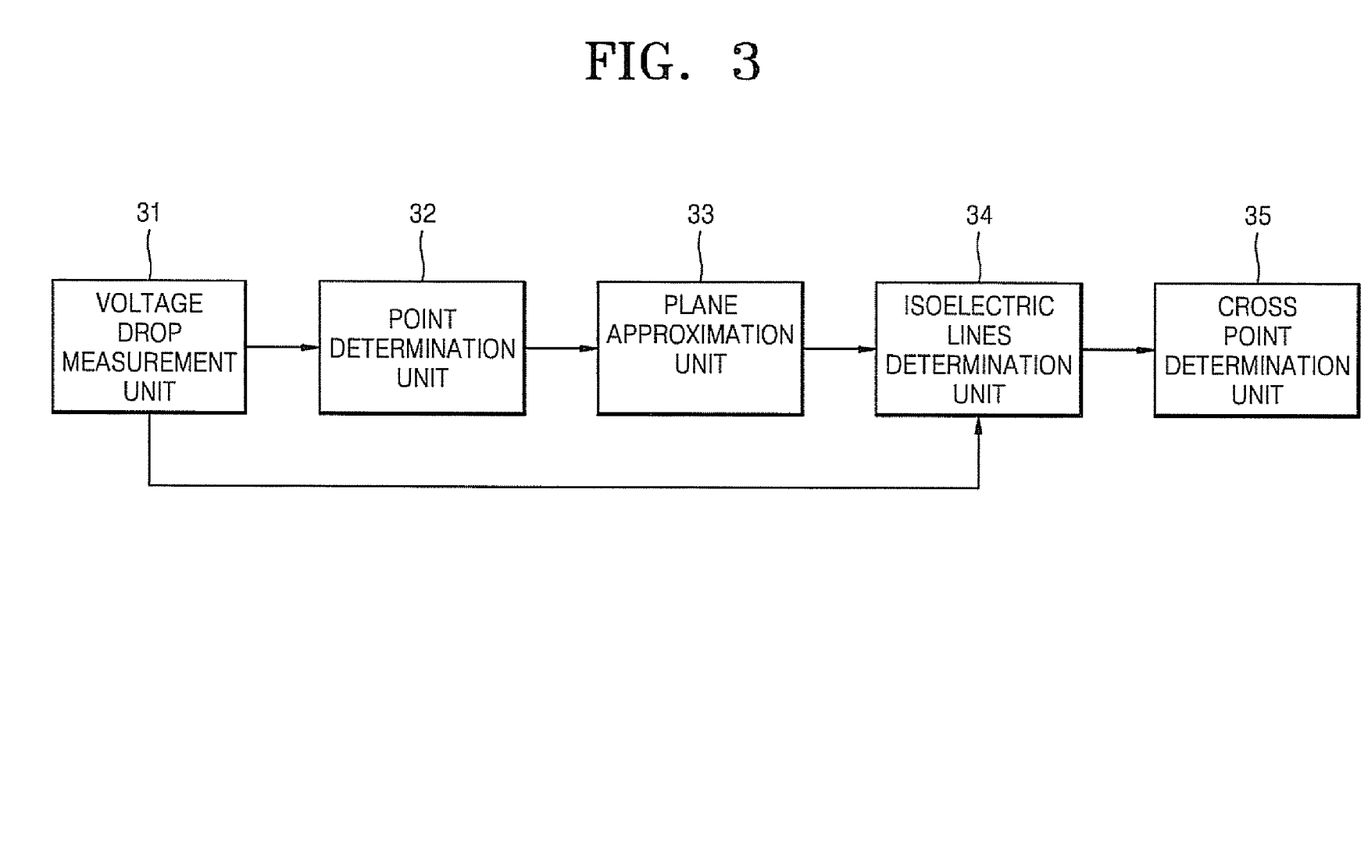
FIG. 3 is a block diagram schematically illustrating an exemplary embodiment of an apparatus for detecting a size and concentration of an ionic material according to the present invention.

FIG. 3 is a block diagram schematically illustrating an exemplary embodiment of an apparatus for detecting a size and concentration of an ionic material according to the present invention.

Referring to FIG. 3, an apparatus includes a voltage drop measurement unit 31, a point determination unit 32, a plane approximation unit 33, an equipotential line determination unit 34 and a cross point determination unit 35.

The voltage drop measurement unit 31 includes at least two FET-based sensors having different electrical characteristics for detecting ionic materials. The voltage drop measurement unit 31 measures voltage drop values of the ionic materials.

In an exemplary embodiment, the voltage drop measurement unit 31 may include at least the two FET-based sensors having different electrical characteristics for detecting ionic materials in a single chamber.

The different electrical characteristics of at least the two FET-based sensors for detecting ionic materials may be obtained through a difference of surface materials of the sensor, a sensor structure and/or a size of the sensor. The difference of the sensor structure may be a relatively slight difference that occurs in a process of manufacturing the same sensor.

In an exemplary embodiment, each FET-based sensor for detecting ionic materials may include a plurality of FET-based sensors having substantially the same electrical characteristics.

The FET can be any of a number of FETs, such as those used in a CMOS device, etc. The FET may be a n-MOS or p-MOS. In one exemplary embodiment, when a substrate of the FET is n-type doped, a source and a drain can be independently p-type doped. Alternatively, when the substrate is p-type doped, the source and drain can be independently n-type doped.

In exemplary embodiments, the FET may include a substrate, a source and a drain that are formed on either side of the substrate and doped to have the opposite polarity to the substrate and a gate formed on the substrate to contact the source and the drain. The source supplies carriers, such as free electrons or holes. The drain is a site which the supplied carriers from the source reach. The gate controls the flow of the carriers between the source and the drain. When detecting an ionic material, such as biomolecule within an electrolyte, a sensor includes the FET because it is able to detect the existence of the ionic material without labeling (Label-free).

In an exemplary embodiment, a chamber including the FET may include an inlet and an outlet for the solution and a micropump for allowing the solution to flow into and out of the chamber.

In the illustrated embodiment, the ionic materials are not particularly limited and may include, but are not limited to, ionic atoms, ion molecules or biomolecules. The biomolecules can be nucleic acid selected from the group consisting of DNA, RNA, PNA, LNA and mixtures thereof, or protein selected from the group consisting of an enzyme, a substrate, an antigen, an antibody, a ligand, an aptamer and a receptor.

In exemplary embodiments, when the ionic material is an ion, the size of the ionic material is defined as the charge of the ion. When the ionic material is nucleic acid, the size of the ionic material is defined as the length of the nucleic acid.

Figure 4:
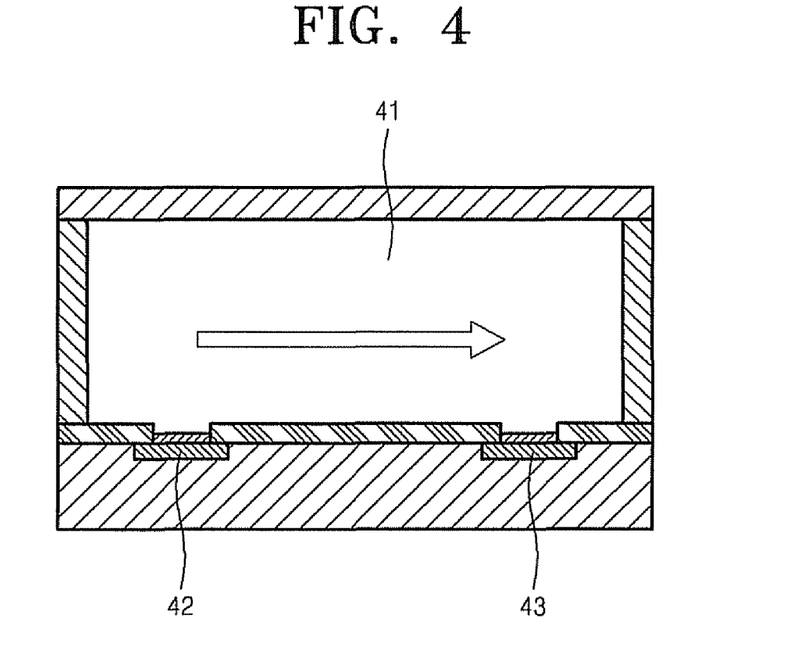
FIG. 4 is a cross-sectional view schematically illustrating an exemplary embodiment of FET-based sensors included in a voltage drop measurement unit of FIG. 3 according to the present invention.

FIG. 4 is a side cross-sectional view schematically illustrating an exemplary embodiment of FET-based sensors included in the voltage drop measurement unit of FIG. 3 according to the present invention. Referring to FIG. 4, two FET-based sensors 42 and 43 having different electrical characteristics for detecting ionic materials are included in a single chamber 41. A sample solution containing ionic materials can flow in the direction of the arrow.

Figure 5:
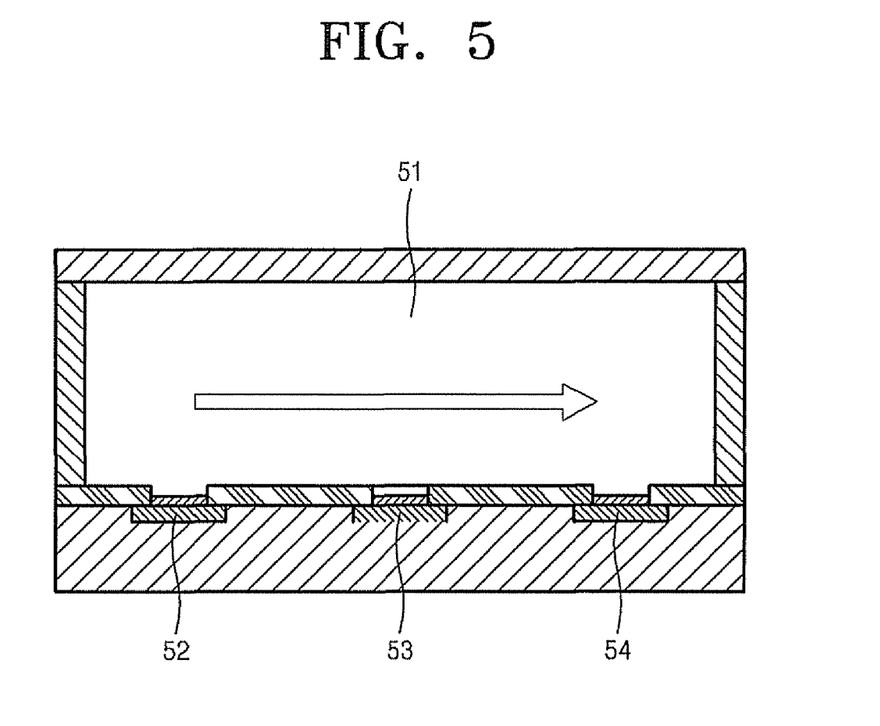
FIG. 5 is a side cross-sectional view schematically illustrating another exemplary embodiment of FET-based sensors included in a voltage drop measurement unit of FIG. 3 according to the present invention.

FIG. 5 is a side cross-sectional view schematically illustrating another exemplary embodiment of FET-based sensors included in the voltage drop measurement unit of FIG. 3 according to the present invention. Referring to FIG. 5, three FET-based sensors 52, 53 and 54 having different electrical characteristics for detecting ionic materials is included in a single chamber 51.

Figure 6:
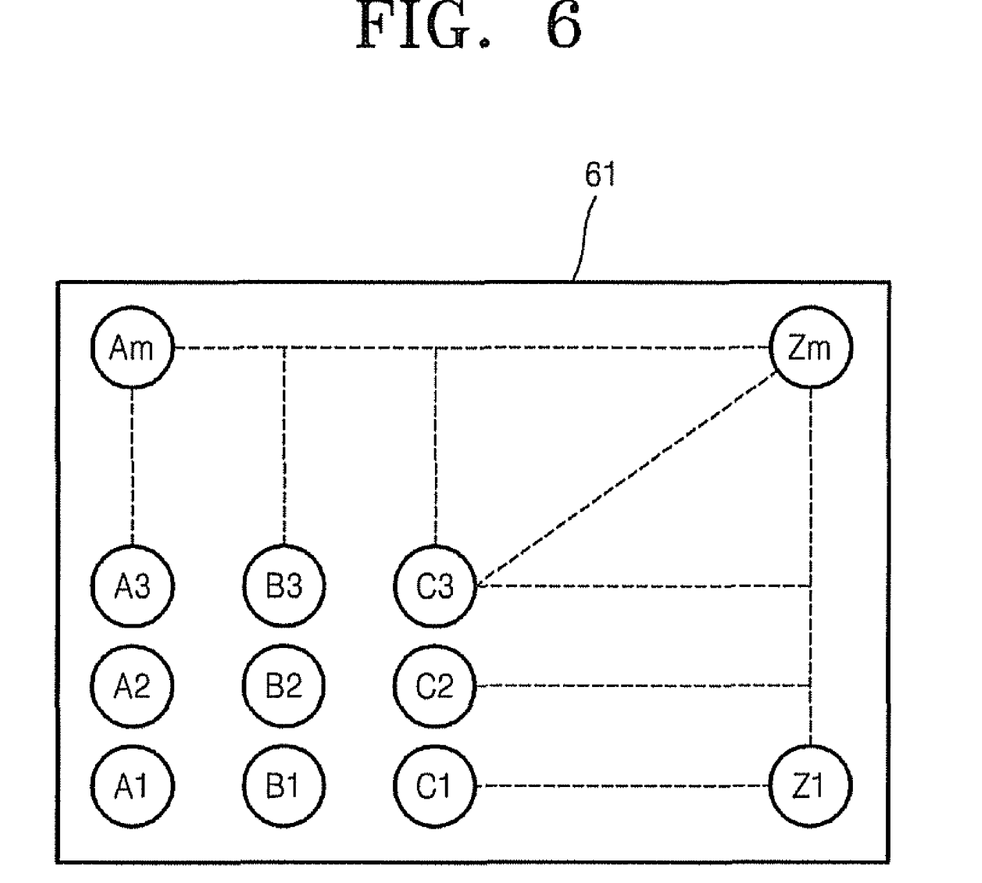
FIG. 6 is a top plane view schematically illustrating another exemplary embodiment of FET-based sensors included in a voltage drop measurement unit of FIG. 3 according to the present invention.

FIG. 6 is a top plane view schematically illustrating another exemplary embodiment of FET-based sensors included in the voltage drop measurement unit of FIG. 3 according to the present invention. Referring to FIG. 6, a plurality of FET-based sensors includes an A group of FET-based sensors (A1,A2,A3, . . . ,Am), a B group of FET-based sensors (B1,B2,B3, . . . ,Bm), a C group of FET-based sensors (C1,C2,C3, . . . ,Cm), etc are included in a single chamber 61. All the FET-based sensors of a single group have the same electrical characteristics, however, different groups of the FET-based sensors have different electrical characteristics.

Referring to FIG. 3, the point determination unit 32 determines points in a three-dimensional plot including a size, a concentration and a voltage drop value from known sizes, concentrations, and voltage drop values of ionic materials The FET-based sensors for detecting ionic materials can independently include a plurality of FET-based sensors having the same electrical characteristics. Calculation of voltage drop values of the ionic materials may be performed by averaging voltage drop values calculated using a plurality of FET-based sensors having the same electrical characteristics.

A determination of equipotential lines that exist on the approximated plane (15) is performed using voltage drop values of the unknown ionic materials with respect to each of at least two FET-based sensors having different electrical characteristics for detecting ionic materials.

In one embodiment, when three points are approximated using a plane, determining the equipotential lines (15) may be performed by substituting z, a voltage drop value of the unknown calculated ionic materials, into Equation 1. By this, an equation comprising two variables of x and y can be obtained.

Then, determination of a cross point between at least the two equipotential lines (16) is performed.

FIG. 2 is a graph illustrating an exemplary embodiment of a process of determining a cross point between equipotential lines according to the present invention. Referring to FIG. 2, equipotential lines are represented on a two-dimensional plane including DNA size base pair ("bp") on the x-axis and concentration on the y-axis. For FET A, 15 mV, 20 mV, 25 mV, 30 mV, and 35 mV equipotential lines are illustrated. For FET B, 12 mV, 14 mV, 16 mV, 18 mV, 20 mV and 22 mV equipotential lines are illustrated.

When voltage drop values of DNA of which size and concentration are unknown with respect to FET A and FET B having different electrical characteristics for detecting ionic materials are 30 mV and 18 mV, respectively, two equipotential lines which cross are obtained and a cross point thereof is determined using the results. An x value and a y value of the cross point refers to the unknown DNA size ("bp") and the unknown DNA concentration, respectively.

Determination of the cross point can be performed such that when at least three equipotential lines exist, cross points between each two equipotential lines of the three equipotential lines are obtained, and an average of the cross points is obtained.

FIG. 3 is a block diagram schematically illustrating an exemplary embodiment of an apparatus for detecting a size and concentration of an ionic material according measured in the voltage drop measurement unit 31.

In the plane approximation unit 33, at least three points determined by the point determination unit 32 are approximated with a single plane.

The plane approximation unit 33 can perform a process of solving constants of a, b and c of Equation 1 using the three points.

$$ax+by+cz+1=0 \qquad \text{Equation (1)}$$

where x refers to size of ionic materials, y refers to concentration and z refers to voltage drop value.

The equipotential line determination unit 34 determines equipotential lines existing on a plane formed in the plane approximation unit 33 using voltage drop value measured in the voltage drop measurement unit 31 of ionic materials of which size and concentration are unknown.

The equipotential line determination unit 34 can perform a process of substituting voltage drop values of the unknown measured ionic materials into Equation 1.

The cross point determination unit 35 determines a cross point between at least two equipotential lines determined by the equipotential line determination unit 34.

The cross point determination unit 35 can perform a process such that when at least three equipotential lines exist, cross points between each two equipotential lines of the three equipotential lines are obtained, and an average point of the cross points is obtained.

Hereinafter, the present invention will be described in further detail with reference to the following examples. These examples are for illustrative purposes only and are not intended to limit the scope of the present invention.

EXAMPLE 1

Manufacture of a FET-Based Biosensor

The FET element used in the current example was customized from X-FAB Semiconductor Foundries (Germany). The customized product is an array in which 48 (4×12) FL FETs manufactured to all have the same structure and electrical characteristics are disposed, and an array in which 192 (12× 16) NMOS FETs manufactured to all have the same structure and electrical characteristics are disposed. However, the structures and electrical characteristics of the NMOS FETs differ from those of the FL FETs. The product was manufactured by using the facility of X-FAB Semiconductor Foundries corp., and by performing the intrinsic CMOS process of the company. The standard CMOS process of each company has slight differences, therefore details thereof are omitted.

By removing a passivation layer and a gate electrode layer of the each FET in the arrays, a polysilicon layer was exposed. Then, the FET surface including the exposed polysilicon layer was carefully washed. The washing was performed with pure acetone and water, and after washing, the resulting products were dried. The substrate washing process used the wet station which is used in a semiconductor manufacturing process. After the washing was over, the product was dried using a spin dry.

A chamber side wall was installed on the array substrate and the substrate was coated with platinum as a standard electrode. A chamber A including 12 FL FETs and 36 NMOS FETs, a chamber B including 12 FL FETs, and a chamber C including 36 NMOS FETs were independently manufactured. As used herein, "FL FET" and "NMOS FET" indicates model names from X-FAB Semiconductor Foundries and/or the inventors based on the FET sizes.

Experimental Example 1

Detecting a Size and Concentration of DNA Using the Illustrated Method

By using each chamber A, B and C manufactured in Example 1, confirmation of whether a size and concentration of a target DNA can be accurately measured was obtained.

DNA having a concentration of 12 ng/µl and a length of 249 bp was used as the target DNA.

1-1: Using Two Different FET Groups

A method according to FIG. 1 was performed using the 12 FL FETs of chamber A as one group and the 36 NMOS FETs of chamber A as another group.

Voltage drop values of three kinds of DNAs, of which length and concentration were known with respect to each group, were measured. Then, voltage drop values of each DNA measured in 12 FL FETs were averaged, and voltage drop values of each DNA measured in 36 NMOS FETs were averaged. Next, 3 points were determined in a three-dimensional plot comprising a length (x), a concentration (y) and voltage drop (z) with respect to the group of FL FETs, and a single plane was approximated from them. In particular, when known sizes and concentrations of the three kinds of DNAs were independently x1, y1; x2, y2; and x3, y3, and measure voltage drop values were z1, z2 and z3, respectively, a plane equation of $a1x+b1y+c1z+1=0$ was obtained by simultaneously solving three equations, that is $a1x1+b1y1+c1z1+1=0$; $a1x2+b1y2+c1z2+1=0$; and $a1x3+b1y3+c1z3+1=0$ and thus determining the values of a, b and c.

Likewise, another plane equation of a2x+b2y+c2z+1=0 was obtained by performing the same method with respect to the group of NMOS FETs.

Thereafter, voltage drop values of target DNAs, of which size and concentration were to be detected with respect to each group, were measured and averaged to obtain z4 and z5, and those values were substituted into the plane equation. Accordingly, two equations of equipotential lines, that is a1x+b1y+c1z4+1=0 and a2x+b2y+c2z5+1=0 were obtained, the two equations were simultaneously solved, and thus x and y values of one cross point were obtained to obtain a size and concentration of the target DNAs.

The results are shown in Table 1.

1-2: Using 12 FETs

A method was performed in the same manner as in Experimental Example 1-1 by individually using each different FET, supposing that each 12 FL FET included the chamber B had little electrical characteristic differences from the manufacturing process.

As a result, 12 equipotential lines and 132 (12×11) cross points were obtained. Accordingly x and y values of the cross points were averaged to obtain a size and concentration of target DNAs. The results are shown in Table 1.

1-3: Using 36 FETs

A method was performed in the same manner as in Experimental Example 1-1 by individually using each different FET, supposing that each 36 NMOS FETs included in the chamber C had little electrical characteristic differences from the manufacturing process.

As a result, 36 equipotential lines and 1,260 (36×35) cross points were obtained. Accordingly x and y values of the cross points were averaged to obtain a size and concentration of target DNAs. The results are shown in Table 1.

1-4: Using 48 FETs

A method was performed in the same manner as in Experimental Example 1-1 by individually using each different FET, supposing that each 12 FL FET and 36 NMOS FET included in the chamber A had little electrical characteristic differences from a manufacturing process.

As a result, 48 equipotential lines and 2,256 (48×47) cross points were obtained. Accordingly x and y values of the cross points were averaged to obtain a size and concentration of target DNAs. The results are shown in Table 1.

TABLE 1

| Example | Experimental | |
|---|---|---|
| | x: length (bp) | y: concentration (ng/μl) |
| 1-1 | 321.067621 | 36.743186 |
| 1-2 | 756.196412 | −13.164146 |
| 1-3 | 124.486370 | 12.876566 |
| 1-4 | 264.433197 | 7.496748 |
| Real length | 249 | 12 |

As shown in Table 1, when examples of the present invention were performed by supposing that little electrical differences had occurred in a process of manufacturing FETs having the same electrical characteristics, the results were not good. On the other hand, when the present invention was performed using FETs having different electrical characteristics, good results were obtained.

The illustrated embodiments can be embodied as computer readable codes on a computer readable recording medium. The computer readable recording medium may be any of a number of data storage devices that can store data which can be thereafter read by a computer system. The computer readable recording medium includes, but is not limited to, read-only memory ("ROM"), random-access memory ("RAM"), CD-ROMs, magnetic tapes, floppy disks, optical data storage devices, and carrier waves (such as data transmission through the Internet).

As in the illustrated exemplary embodiments, a concentration and a size of ionic materials, such as nucleic acid, can be simultaneously measured. When target ionic materials are detected using FET-based biosensors, not only can a concentration of ionic materials according to a change in voltage or current be confirmed, but also whether the change in voltage or current can be contributed to the target ionic materials can be confirmed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting a size and concentration of an ionic material, the method comprising:

measuring voltage drop values of at least three kinds of ionic materials of which sizes and concentrations are known, the measuring voltage drop values including using each of at least two FET-based sensors having different electrical characteristics for detecting ionic materials;

determining at least three points in a three-dimensional plot including a size, a concentration and a voltage drop value from the known sizes, concentrations, and the measured voltage drop values of the at least three kinds of ionic materials with respect to the each of at least the two FET-based sensors having different electrical characteristics for detecting ionic materials;

approximating the at least three determined points to a single plane with respect to the each of at least two FET-based sensors having different electrical characteristics for detecting the ionic materials;

measuring a voltage drop value of an ionic material of which size and concentration are unknown, the measuring a voltage drop value including using the each of at least two FET-based sensors having different electrical characteristics for detecting the ionic materials;

determining equipotential lines existing on the plane using the voltage drop value of unknown ionic material with respect to the each of at least two FET-based sensors having different electrical characteristics for detecting the ionic materials; and determining at least one cross point between the determined equipotential lines.

2. The method of claim 1, wherein the measuring voltage drop values includes introducing a solution containing each of the at least three ionic materials into a chamber including the at least two FET-based sensors having different electrical characteristics for detecting the ionic materials.

3. The method of claim 1, wherein the different electrical characteristics of at the least two FET-based sensors for detecting ionic materials are obtained through a difference of materials on a surface of the sensor, a sensor structure or a size of the sensor.

4. The method of claim 1, wherein the each of at least two FET-based sensors for detecting ionic materials includes a plurality of FET-based sensors having same electrical characteristics.

5. The method of claim 4, wherein the measuring voltage drop values includes averaging the voltage drop values measured using the plurality of FET-based sensors having the same electrical characteristics.

6. The method of claim 1, wherein the size of the ionic materials is a charge or a length of the ionic materials.

7. The method of claim 1, wherein the approximating to a single plane includes solving constants of a, b and c of Equation 1 using three points:

$$ax+by+cz+1=0 \qquad \text{Equation (1)}$$

where x refers to size of ionic material, y refers to concentration and z refers to voltage drop value.

8. The method of claim 7, wherein the determining equipotential lines includes substituting the voltage drop value of the unknown measured ionic material into Equation 1.

9. The method of claim 1, wherein the determining at least one cross point between the equipotential lines includes obtaining cross points between each two equipotential lines of the equipotential lines and obtaining an average point of the cross points.

10. The method of claim 1, wherein the ionic materials are biomolecules.

11. The method of claim 10, wherein the biomolecules are nucleic acids or proteins.

12. An apparatus for detecting a size and concentration of ionic materials, the apparatus comprising:
- a voltage drop measurement unit including at least two FET-based sensors having different electrical characteristics for detecting ionic materials;
- a point determination unit determining points in a three-dimensional plot including a size, a concentration and a voltage drop value from known sizes, concentrations and voltage drop values, respectively, of ionic materials measured in the voltage drop measurement unit;
- a plane approximation unit approximating at least three of the points determined in the point determination unit into a single plane;
- an equipotential line determination unit determining equipotential lines existing on the plane approximated in the plane approximation unit, the determining equipotential lines using the voltage drop values measured in a voltage drop measurement unit of ionic materials of which size and concentration are unknown; and
- a cross point determination unit determining a cross point between at least two equipotential lines determined in the equipotential line determination unit.

13. The apparatus of claim 12, wherein the voltage drop measurement unit comprises the at least two FET-based sensors having different electrical characteristics for detecting ionic materials in a single chamber.

14. The apparatus of claim 12, wherein the different electrical characteristics of the at least two FET-based sensors for detecting ionic materials are obtained through a difference of materials on a surface of the sensor, a sensor structure or a size of the sensor.

15. The apparatus of claim 12, wherein the each of at least two FET-based sensors for detecting ionic materials includes of a plurality of FET-based sensors having the same electrical characteristics.

16. The apparatus of claim 12, wherein the size of the ionic materials is a charge or length of the ionic materials.

17. The apparatus of claim 12, wherein the plane approximation unit solves constants of a, b and c of Equation 1 using three points:

$$ax+by+cz+1=0 \qquad \text{Equation (1)}$$

where x refers to size of ionic materials, y refers to concentration and z refers to voltage drop value.

18. The apparatus of claim 17, wherein the equipotential line determination unit substitutes the voltage drop value of the unknown measured ionic material into Equation 1.

19. The apparatus of claim 12, wherein the cross point determination unit obtains cross points between each two equipotential lines of the determined equipotential lines when at least three equipotential lines exist and obtains an average point of the cross points.

20. The apparatus of claim 12, wherein the ionic materials are biomolecules.

* * * * *